United States Patent
Christiansen et al.

(10) Patent No.: US 9,965,591 B2
(45) Date of Patent: May 8, 2018

(54) PHYSIOLOGIC SIMULATOR SYSTEM

(75) Inventors: Dean Christiansen, Minneapolis, MN (US); Joseph Morrow, Minneapolis, MN (US); Charles Tabor, St. Cloud, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 1092 days.

(21) Appl. No.: 14/343,043

(22) PCT Filed: Sep. 13, 2012

(86) PCT No.: PCT/US2012/055141
§ 371 (c)(1),
(2), (4) Date: Jun. 17, 2014

(87) PCT Pub. No.: WO2013/040195
PCT Pub. Date: Mar. 21, 2013

(65) Prior Publication Data
US 2015/0161347 A1    Jun. 11, 2015

Related U.S. Application Data

(60) Provisional application No. 61/533,853, filed on Sep. 13, 2011.

(51) Int. Cl.
*G09B 23/28* (2006.01)
*G06F 19/00* (2018.01)
(Continued)

(52) U.S. Cl.
CPC .......... *G06F 19/3437* (2013.01); *G06F 19/12* (2013.01); *G09B 23/285* (2013.01);
(Continued)

(58) Field of Classification Search
USPC ................................. 434/262, 267, 268, 272
See application file for complete search history.

(56) References Cited

U.S. PATENT DOCUMENTS 3,376,659 A  *  4/1968  Asin ................... G09B 23/285
                                                    434/272
4,726,772 A  *  2/1988  Amplatz ............. G09B 23/285
                                                    434/272
(Continued)

FOREIGN PATENT DOCUMENTS

WO      WO92/19199          11/1992
WO      WO2013/040195 A2    3/2013
WO      WO2013/040195 A3    3/2013

OTHER PUBLICATIONS

PCT/US2012/055141, PCT International Preliminary Report on Patentability.

(Continued)

*Primary Examiner* — Kurt Fernstrom
(74) *Attorney, Agent, or Firm* — Medler Ferro Woodhouse & Mills PLLC

(57) ABSTRACT

Systems (10) for the simulation of percutaneous medical procedures are disclosed. The systems can include a simulated vasculature including a first component (24) configured to allow for introduction of a medical device into the system through an introductory port, a second component (14) connected to the first component and shaped to simulate a portion of a human vasculature, and a third component (18) connected to the second component and shaped to simulate a delivery site for the medical procedure. The system can be configured to allow for a medical device to be delivered to the third component by passing through the introductory port of the first component and passing through the second component. The system can be configured to replicate simulated conditions of use for the medical procedure. Methods for simulating a percutaneous medical procedure using a simulated vasculature are also disclosed.

44 Claims, 7 Drawing Sheets

(51) Int. Cl.
*G09B 23/30* (2006.01)
*G09B 23/34* (2006.01)
*G06F 19/12* (2011.01)
*A61B 17/00* (2006.01)

(52) U.S. Cl.
CPC ........... *G09B 23/303* (2013.01); *G09B 23/34* (2013.01); *A61B 17/00234* (2013.01); *A61B 2017/0084* (2013.01); *A61B 2017/0092* (2013.01); *A61B 2017/00243* (2013.01); *A61B 2017/00716* (2013.01); *A61B 2017/00778* (2013.01); *A61B 2017/00907* (2013.01); *F04C 2270/0421* (2013.01)

(56) References Cited

U.S. PATENT DOCUMENTS

| | | | | |
|---|---|---|---|---|
| 5,112,228 | A * | 5/1992 | Zouras | G09B 23/285 434/267 |
| 6,824,389 | B1 | 11/2004 | Garrett, Jr. et al. | |
| 7,648,367 | B1 * | 1/2010 | Makower | G09B 23/285 434/262 |
| 7,993,140 | B2 * | 8/2011 | Sakezles | G09B 23/306 434/267 |
| 8,439,687 | B1 * | 5/2013 | Morriss | G09B 23/285 434/267 |
| 8,678,830 | B2 * | 3/2014 | Gurdin | G09B 23/30 434/262 |
| 8,808,004 | B2 * | 8/2014 | Misawa | G09B 23/30 434/268 |
| 8,911,238 | B2 * | 12/2014 | Forsythe | G09B 23/28 434/267 |
| 8,944,825 | B2 * | 2/2015 | Reid-Searl | G09B 23/30 434/267 |
| 2005/0130107 | A1 | 6/2005 | Ellingson et al. | |
| 2005/0202381 | A1 | 9/2005 | Keegan | |
| 2007/0269784 | A1 | 11/2007 | LaFrance et al. | |
| 2009/0226867 | A1 | 9/2009 | Kalafut et al. | |

OTHER PUBLICATIONS

Sulaiman et al. "Invitro non-rigid life-size model of Arotic Arch Aneurysm for Endovascular Prosthesis Assessment" European Journal of Cardio-Thoracic Surgery, Springer Verlag Berling DE vol. 33, No. 1, Nov. 28, 2007, pp. 53-57.

Toshio Fukuda et al. "Social Impact of In-Vitro Endovascular Surgery Simulation Technology" Advanced Robotics and its Social Impacts, 2010 IEEE Workshop on, IEEE, Piscataway, NJ, USA, Oct. 26, 2010, pp. 142-147.

* cited by examiner

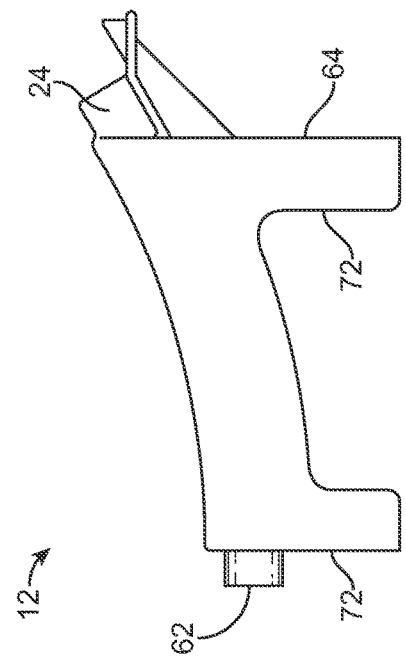
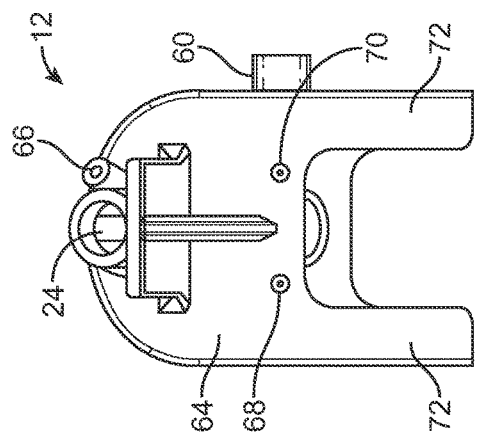
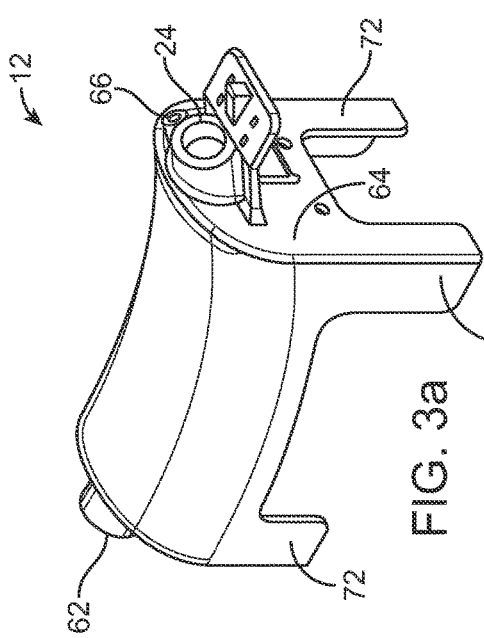
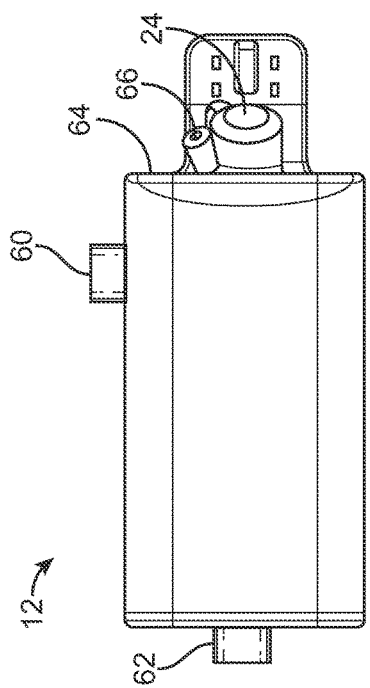

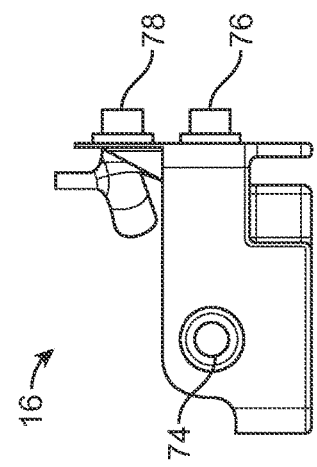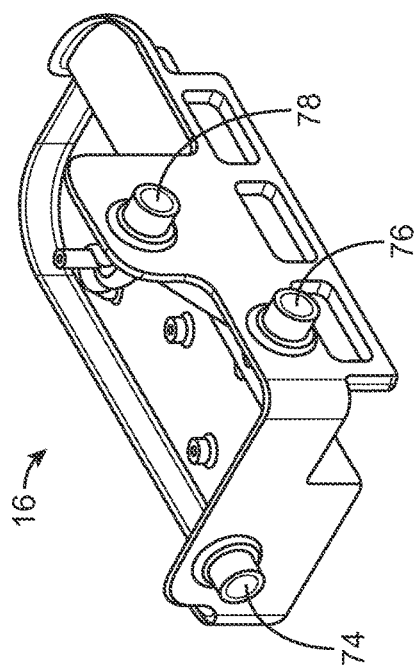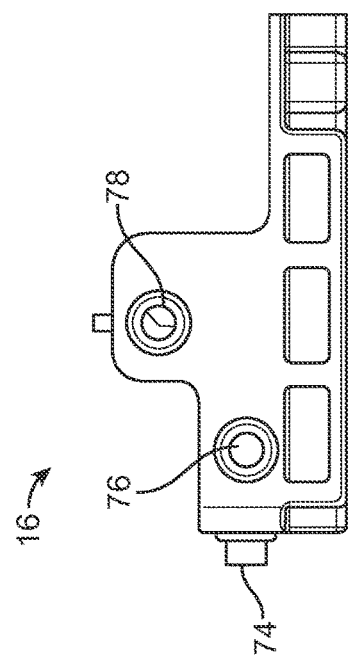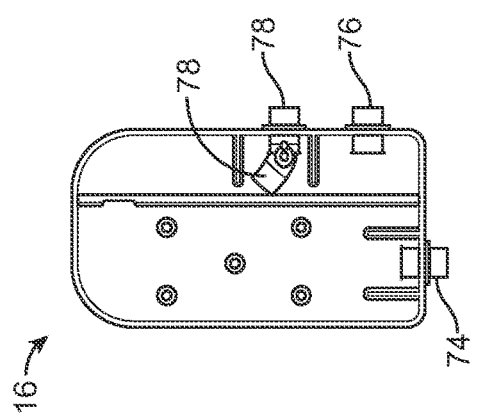
FIG. 4b
FIG. 4d
FIG. 4a
FIG. 4c

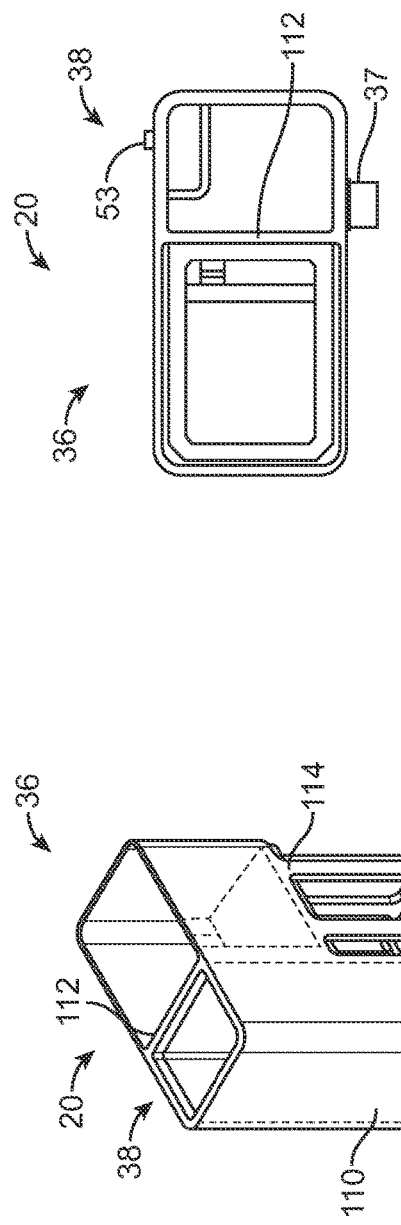
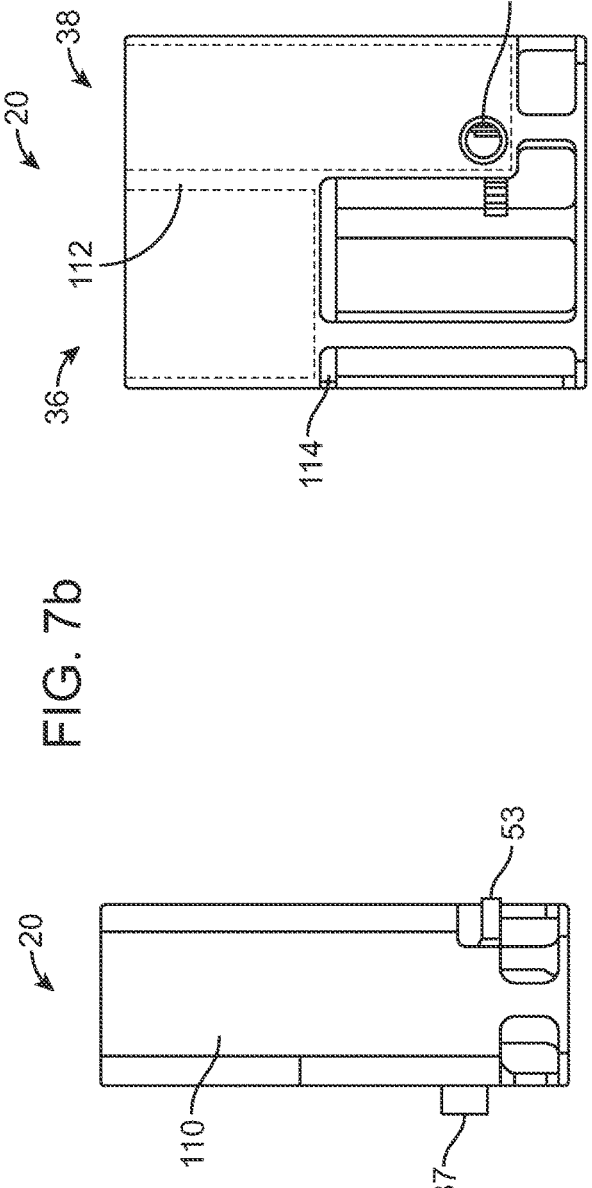
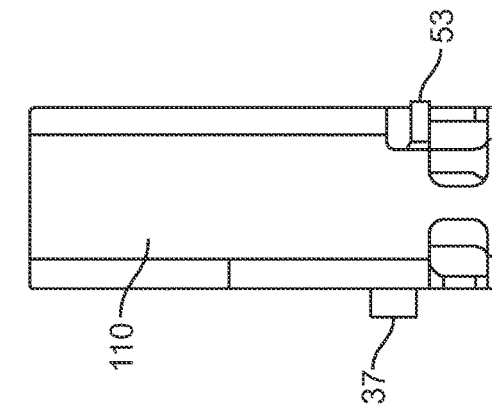
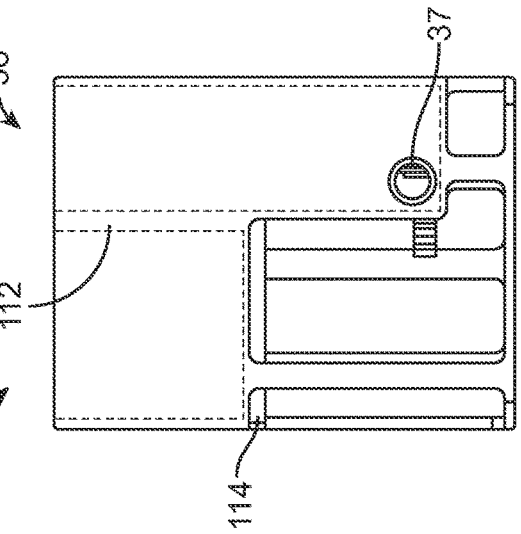
FIG. 7a
FIG. 7b
FIG. 7c
FIG. 7d

PHYSIOLOGIC SIMULATOR SYSTEM

BACKGROUND

Field

Certain embodiments of the present invention are related to physiologic simulator systems for medical procedures.

Background Art

Medical devices can be delivered to a site within a patient through a variety of techniques. For example, a medical device can be implanted or otherwise delivered through conventional open surgical techniques, such as for example open-heart surgery. In some techniques, a medical device can be implanted or delivered percutaneously. For example, in some percutaneous techniques, a medical device, such as a valve prosthesis can be compacted and loaded onto a delivery device for advancement through a patient's vasculature in a transfemoral, transapical, or transatrial procedure. There is a continuous need for physiologic simulator systems that can be used for training or other purposes related to catheter-based medical procedures as well as other delivery techniques.

SUMMARY

In some embodiments, a system for the simulation of percutaneous medical procedures can include a simulated vasculature including a first component configured to allow for introduction of a medical device into the system through an introductory port, a second component connected to the first component and shaped to simulate a portion of a human vasculature, and a third component connected to the second component and shaped to simulate a delivery site for the medical procedure. The system can be configured to allow for a medical device to be delivered to the third component by passing through the introductory port of the first component and passing through the second component. The system can be configured to replicate simulated conditions of use for the medical procedure.

In some embodiments, a method of simulating a percutaneous medical procedure can include using a simulated vasculature having a first component configured to allow for introduction of a medical device into the system through an introductory port, a second component connected to the first component and shaped to simulate a portion of a human vasculature, and a third component connected to the second component and shaped to simulate a delivery site for the medical procedure. The method can include inserting a medical device into the introductory port of a first component, advancing the medical device through the first component and into a second component, and advancing the medical device through the second component and into a third component.

BRIEF DESCRIPTION OF THE DRAWINGS/FIGURES

The accompanying figures, which are incorporated herein, form part of the specification and illustrate embodiments of a physiologic simulator system. Together with the description, the figures further serve to explain the principles of and to enable a person skilled in the relevant art(s) to make and use the systems described herein.

Figure 1:
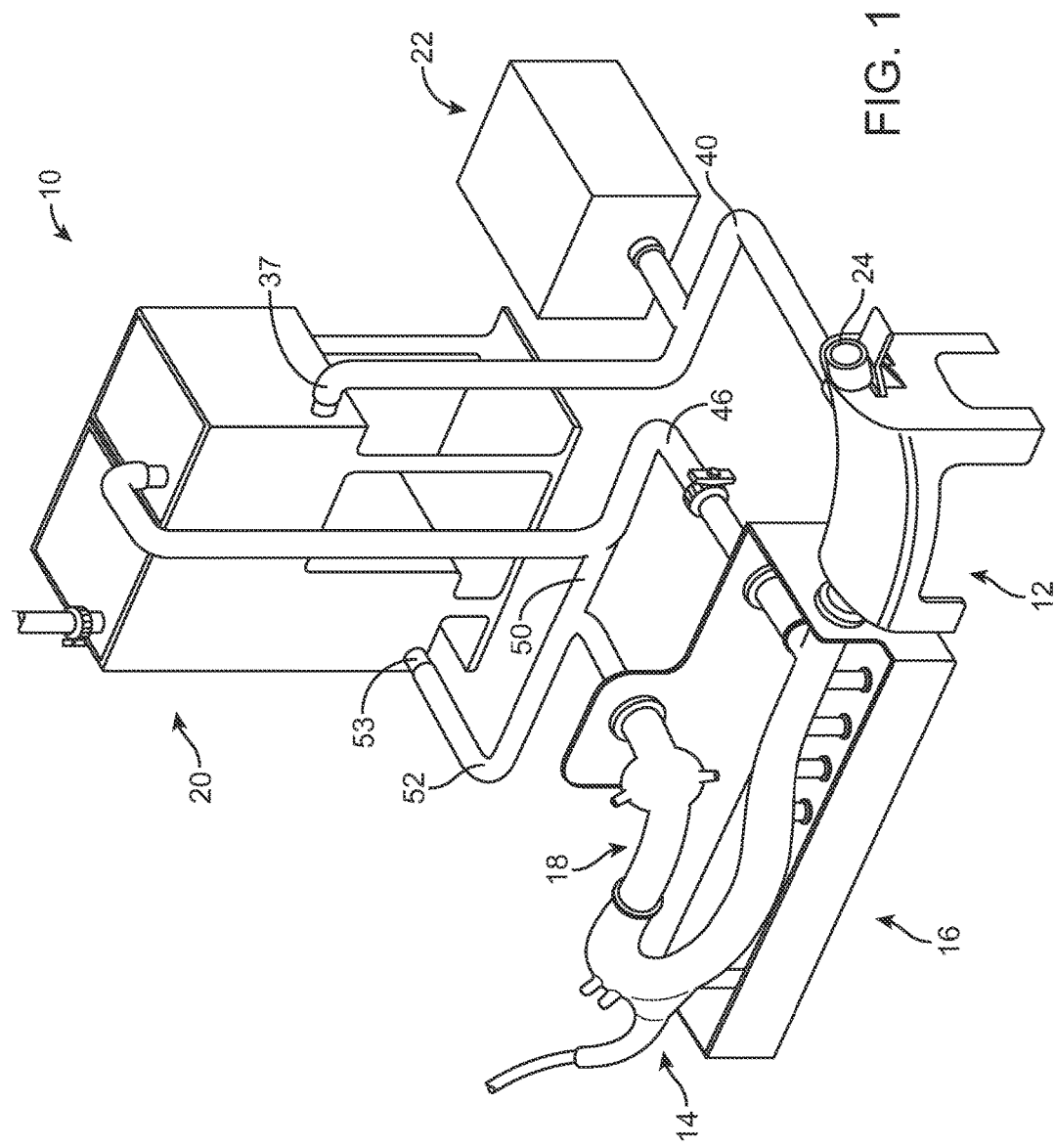
FIG. 1 illustrates an embodiment of a physiologic simulator system.

FIGS. 3a-d illustrate various views of an embodiment of a first component of the system of FIG. 1.

FIGS. 4a-d illustrate various views of an embodiment of a base of the system of FIG. 1.

FIGS. 5a-d illustrate various views of an embodiment of a second component of the system of FIG. 1.

Figure 6C:
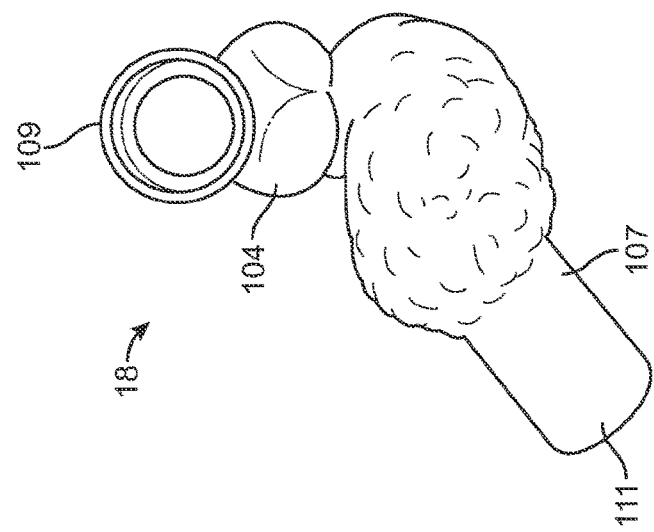
Figure 6B:
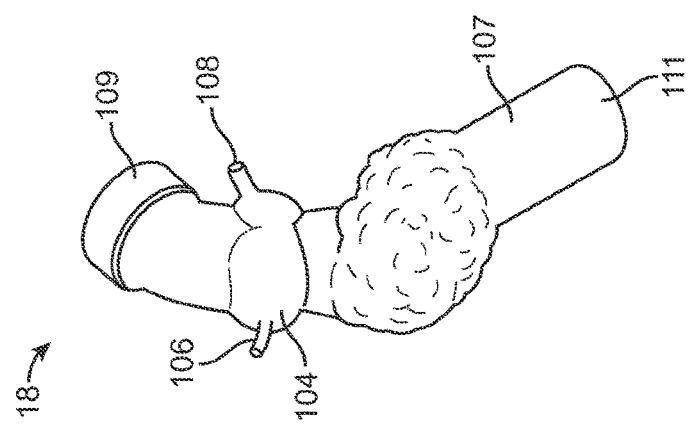
Figure 6A:
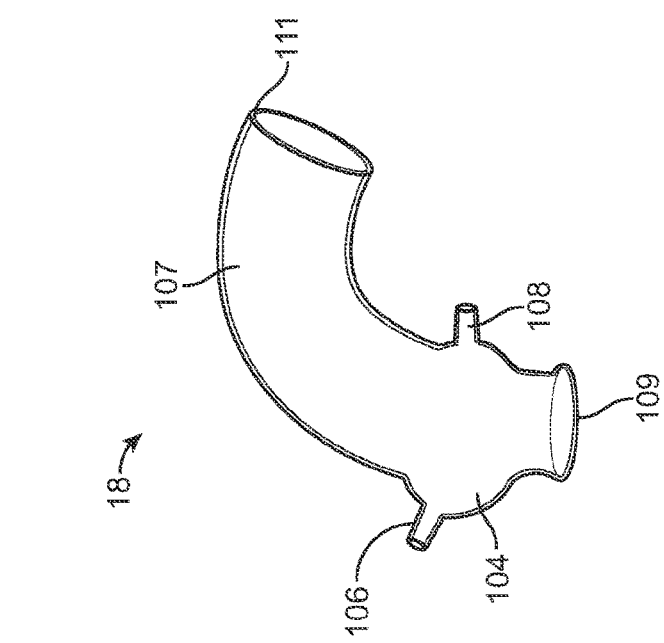

FIG. 6a illustrates a view of an embodiment of a third component of the system of FIG. 1.

FIGS. 6b-c illustrate various views of another embodiment of a third component of the system of FIG. 1.

FIGS. 7a-d illustrate various views of an embodiment of a tank unit of the system of FIG. 1.

DETAILED DESCRIPTION

The following detailed description refers to the accompanying figures which illustrate several embodiments. Other embodiments are possible. Modifications can be made to the embodiments described herein without departing from the spirit and scope of the present invention. Therefore, the following detailed description is not meant to be limiting.

FIG. 1 illustrates an embodiment of a physiologic simulator system 10. In some embodiments, system 10 can enable an operator to perform one or more catheter-based implant procedures under simulated conditions of use. System 10 can include a first component 12, a second component 14 supported by a base 16, third component 18, tank unit 20, and a pump 22, each of which is described further herein.

As shown in FIG. 1, first component 12 can include an introducer port 24 which can allow for the introduction of a device (not shown), such as a delivery catheter. First component 12 is operatively connected to second component 14 to allow the device to pass through first component and be received within second component 14. Second component 14 is operatively connected to third component 18 to allow the device to pass through second component 14 and be received within third component 18. Base 16 can include one or more ports, described, for example, in FIGS. 4a-d, which can serve to connect first component 12 and second component 14 and/or second component and third component 18. In some embodiments, one or more of the components can be constructed or suitably joined to form a single monolithic component. For example, in some embodiments, second component 14 and third component 18 are a single monolithic component. In some embodiments, first component 12 and second component 14 are a single monolithic component. In some embodiments, first component 12, second component 14, and third component 18 are a single monolithic component.

First component 12, second component 14, and third component 18 can be fluidly connected to tank unit 20 and pump 22 to simulate fluid flow within system 10. In some embodiments, the fluid can be human blood or animal blood. In certain embodiments, the blood has been processed, for example, to remove clotting factors. In some embodiments, system 10 can have a closed flow path for fluid. In some embodiments, the fluid can be water, which can, for example, be used to simulate blood. In some embodiments and as described further herein, one or more hemostats, clamps, and/or valves can be used to adjust pressures and flow rates within system 10. In some embodiments, one or more components of system 10 can be immersed or otherwise disposed within a volume of fluid when fully assembled.

System 10 can allow assessment of various measures which can be relevant to percutaneous aortic valve (PAV)

procedures, such as hemodynamic performance (e.g., pressures, cardiac output, paravalvular leakage and the like). System 10 can additionally or alternatively be used for training. Such training can include, for example, assessment of coronary occlusion and flow, as well as implant positioning parameters such as placement depth, rotational orientation, vascular dissection and/or anterior mitral leaflet interference.

In some embodiments, the system can be used as a training tool in the field. In some embodiments, the system can be used for planned interventional procedures. In some embodiments, the system can be used to simulate procedures for relatively difficult or unusual cases. For example, in cases where uncommon anatomy is known to be present, a simulator corresponding to such anatomy can be used. One example of such an uncommon anatomy can include certain cases of aortic valve replacement. For example, approximately 1-2% of the population have two aortic valve cusps rather than three aortic valve cusps. One or more components of system 10 can be configured to simulate such uncommon anatomy.

In some embodiments, system 10 can be used to simulate one or more percutaneous delivery procedures. In some percutaneous techniques, a valve prosthesis can be compacted and loaded onto a delivery device for advancement through a patient's vasculature. In some embodiments, system 10 can allow for simulation of illiofemoral, apical, direct aortic, and subclavianiaxillary entry locations in a single apparatus. System 10 can be configured to allow access from multiple locations per procedure (e.g. bilateral femoral access). In some embodiments, system 10 can simulate a delivery of a valve prosthesis, such as a heart valve prosthesis, through an artery or vein, a femoral artery, a femoral vein, a jugular vein, a subclavian artery, an axillary artery, an aorta, an atrium, and/or a ventricle. System 10 can simulate a delivery of a valve prosthesis via a transfemoral, transapical, transseptal, transatrial, transventrical, or transaortic procedure.

In some embodiments, a heart valve prosthesis that can be used in a simulated delivery with system 10 can include a frame that supports a prosthetic valve body. The valve body can be formed, for example, from one or more a biocompatible synthetic materials, synthetic polymers, an autograft tissue, homograft tissue, xenograft tissue, or one or more other suitable materials. The valve body can be formed, for example, from bovine, porcine, equine, ovine, and/or other suitable animal tissues. The valve body can be formed, for example, from heart valve tissue, pericardium, and/or other suitable tissue. The valve body can comprise one or more valve leaflets, for example, the valve body may be a tri-leaflet bovine pericardium valve, a bi-leaflet valve, or another suitable valve.

System 10 can be used to simulate a transfemoral delivery procedure. In one example of a transfemoral delivery procedure in vivo, a delivery device in the form of a valve prosthesis can be advanced in a retrograde manner through a patient's femoral artery and into the patient's descending aorta. A catheter can then be advanced under fluoroscopic guidance over the simulated aortic arch, through the ascending aorta, into the left ventricle, and mid-way across the defective aortic valve. Once positioning of the catheter is confirmed, the delivery device can deploy the valve prosthesis within the valve annulus. The valve prosthesis can then expand against the simulated annulus. In some embodiments, as the valve prosthesis is expanded, it can trap leaflets against the annulus, which can retain the native valve in a permanently open state. In system 10, first component 12 can simulate a patient's access anatomy and femoral artery. Second component 14 can simulate the patient's descending aorta, aortic arch, and a portion of the ascending aorta. Third component 18 can simulate a portion of the patient's ascending aorta, as well as the left ventricle, aortic valve, and valve annulus.

In some embodiments, system 10 can simulate a transapical delivery procedure. In one example of a transapical procedure in vivo, a trocar or overtube can be inserted into a patient's left ventricle through an incision created in the apex of the patient's heart. A dilator can be used to aid in the insertion of the trocar. In this approach, the native valve (for example, the mitral valve) can be approached downstream relative to blood flow. The trocar can be retracted sufficiently to release the self-expanding valve prosthesis. The dilator can be presented between the leaflets. The trocar can be rotated and adjusted to align the valve prosthesis in a desired alignment. The dilator can be advanced into the left atrium to begin disengaging the proximal section of the valve prosthesis from the dilator. In some transapical embodiments, one or more components, such as for example second component 14 can be omitted and third component 18 can be directly fluidly connected to another component, which can provide a closed fluid loop for system 10.

In some embodiments, system 10 can simulate a transatrial delivery procedure. In one example of a transatrial procedure in vivo, a dilator and trocar can be inserted through an incision made in the wall of the left atrium of the heart. The dilator and trocar can then be advanced through the native valve and into the left ventricle of heart. The dilator can then be withdrawn from the trocar. A guide wire can be advanced through the trocar to the point where the valve prosthesis comes to the end of the trocar. The valve prosthesis can be advanced sufficiently to release the self-expanding frame from the trocar. The trocar can be rotated and adjusted to align the valve prosthesis in a desired alignment. The trocar can be withdrawn completely from the heart such that the valve prosthesis self-expands into position and can assume the function of the native valve.

In some embodiments, one or more components of the system can be portable. In some embodiments, the entire system can be portable. In some embodiments, the components of system 10 can be disassembled and packaged together, which can allow for easy transport of system 10 to a training site or other location. In some embodiments, system 10 can be transported in a hand-carried case of approximately 1 cubic meter or less. In some embodiments, one or more of the components can be assembled and form a semi-permanently or permanently assembled system that is not portable. In some embodiments, system 10 can be assembled for use on a table top.

In some embodiments, system 10 can include conduits, such as conduits 40, 46, 50, 52, and 56 (shown in FIG. 1 and/or FIG. 2) and valves, such as valves 48 and 54, which can fluidly connect one or more of the components. In some embodiments, the conduits can be in the form of quick-connect fittings. In some embodiments, one or more of the components can be connected via one or more tubing connections.

In some embodiments, the use of multiple components to be assembled together can allow for the components to be independently cleaned and/or sterilized. For example, in some embodiments, one component can be constructed from a different material than another component and may require different cleaning and/or sterilization techniques. In some embodiments, one or more components of system 10 can be cleaned and/or sterilized together while assembled.

In some embodiments, one or more components of system 10 are in the form of interchangeable parts. As merely one example, in some embodiments, third component 18 can include a simulated heart valve with 3 leaflets, whereas in some embodiments, third component 18 can include a simulated heart valve with 2 leaflets. In some embodiments, the use of interchangeable parts can allow for easy and quick modification of system 10 to allow for various configurations and/or alternative conditions. As another example, an interchangeable component identical to third component 18 can be used to allow repeated training on a single configuration. In some embodiments, first component 12 can be interchangeable. In some embodiments, second component 14 can be interchangeable.

In some embodiments, one or more of the components can be secured or attached through various types of fasteners. For example, second component 14 can be attached to third component 18 with cable ties. The attachment can be performed by a rapid tensioning tool. In some cases, such table ties can be easily cut and discarded to allow one or more components of system 10 to be removed. In some embodiments, one or more components of system 10 can be removed and replaced to allow for a procedure to be repeated.

In some embodiments, one or more components or portions of the components can be partially or completely transparent. In some embodiments, this can allow for one or more portions of the procedure to be visualized by an operator or observer. Some embodiments of the system can allow for one or more portions of the system to be visualized using fluoroscopy or other suitable visualization techniques. In some embodiments, a procedure can be visualized and performed under fluoroscopy with dye contrast.

Figure 2:
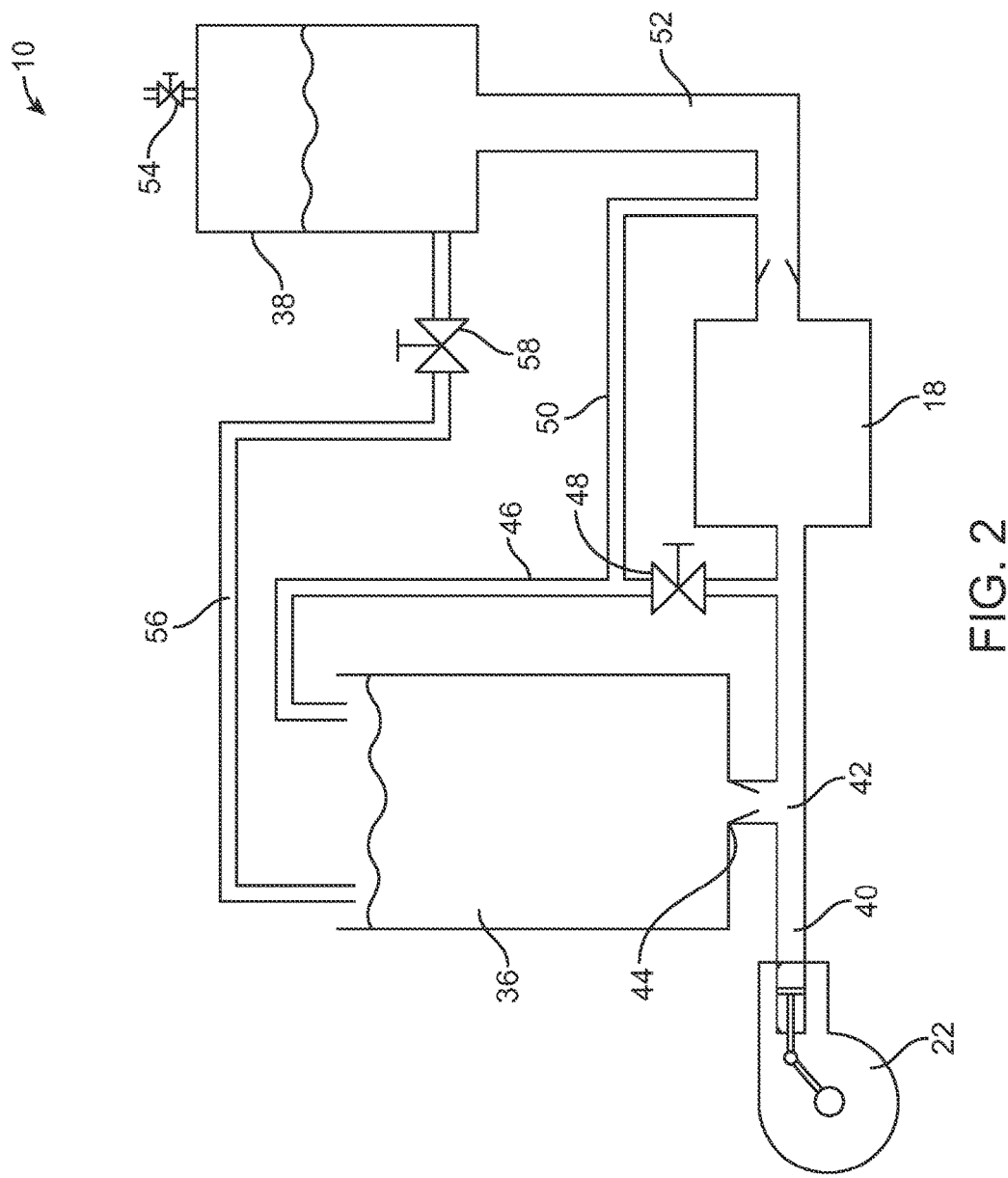
FIG. 2 is a schematic flow diagram of the system of FIG. 1.

FIG. 2 is a schematic flow diagram of system 10. FIG. 2 diagrams pump 22, third component 18, a first tank 36, and a second tank 38 (first tank 36 and second tank 38 together make up tank unit 20 shown in FIG. 1), as well as various valves, conduits, and junctions disposed therebetween. As shown in FIG. 2, a conduit 40, which can be in the form of a pump hose, connects pump 22 to first tank 36 at port 37 located on first tank 36 and a first end of third component 18 via a T-junction 42. In some embodiments, conduit 40 can simulate a left atrium of a human heart.

A one-way valve 44 can be disposed between first tank 36 and pump 22. In some embodiments, valve 44 can be configured to simulate a mitral valve. Valve 44 can, for example, be a Medtronic Hall® brand single leaflet mechanical prosthetic valve (developed by Medtronic, Inc.). In some embodiments, a suture ring can be removed from such a valve, in some cases, this can allow valve 44 to be mounted directly and permanently into a bottom surface of the tank. Any suitable valve design can be used. For example, a suitable mitral or aortic valve replacement, including a bi-leaflet design or tri-leaflet design, could be used. In some embodiments, a mechanical valve can be used. In some embodiments, system 10 can include an extended plug that can cover the orifice of valve 44 when desired.

In some embodiments, a top end of first tank 36 can be left open to the atmosphere. Conduit 40 can be connected to another conduit 46 via valve 48, which can serve as a "fast pace" bypass conduit. In some embodiments, valve 48 can be closed to simulate normal cardiac output and opened when desired to simulate a reduction in cardiac output possible for a "fast pacing" mode. That is, when valve 48 is open, it can simulate reduced pressure and cardiac output from a ventricle, which can hydrodynamically simulate fast pacing of a human heart. An output end of third component 18 can be fluidly connected to first tank 36 as well as second tank 38 via respective conduits 50 and 52. Conduit 52 can connect to second tank 38 via port 53. In some embodiments, second tank 38 is sealed and can include a valve 54 which can allow an operator to increase or decrease an amount of fluid and/or pressure within second tank 38. In some embodiments, second tank 38 can be fluidly connected to first tank 36 via conduit 56. A valve 58 can be located along conduit 56 can be a valve 58 which can restrict the flow between second tank 38 and first tank 36.

FIGS. 3a-d illustrate various views of first component 12. FIG. 3a illustrates a front perspective view of first component 12. FIG. 3b illustrates a front view of first component 12. FIG. 3c illustrates a top view of first component 12. FIG. 3d illustrates a right side view of first component 12. In some embodiments, first component 12 can be shaped to simulate anatomy. In some embodiments, first component 12 is not shaped to simulate anatomy.

In some embodiments, first component 12 can simulate a patient's access anatomy and femoral artery. For example, first component 12 can allow for the introduction of a device such as a delivery catheter to system 10. First component 12 can be operatively connected to base 16 to allow the device to pass through first component 12 and be received within base 16. In some embodiments, first component 12 can be connected to second component 14 without passing through base 16. In some embodiments, first component 12 can include a port 60 fluidly connected to first tank 36 and pump 22 and a second port 62 fluidly connected to a port on base 16.

First component 12 can be in the form of a simulated leg model or other desired anatomy. One embodiment of a suitable leg model is shown for example in FIG. 3. In some embodiments, first component 12 can represent the continuation of a patient's descending aorta inferior to thoracic aorta. As illustrated, first component 12 can be generally curved and elevated at one end 64, which can correspond to an inferior direction towards a patient's legs.

In some embodiments, first component 12 can include one or more inlet ports, such as introducer ports 24 and 66, which can represent separate locations for introduction of separate devices, such as a guidewire and separate delivery catheter. In some embodiments, introducer ports 24 and 66 can model left and right femoral arteries as separate introduction sites. In some embodiments, first component 12 can include a tray, which can for example be in the form of a small open tank, which can be placed under introducer ports 24 and 66. In some embodiments, the tray can collect small amounts of water that may drip from the ports. In some embodiments, a tray can be integrated into the first component 12.

In some embodiments, first component 12 can include one or more openings 68 and 70, which can be configured to hold excess lengths of guidewire. In some embodiments, first component 12 can include one or more legs 72, which can support first component 12 and/or elevate first component 12 to a desired height or angle. In some embodiments, one or more legs 72 of first component 12 can be adjustable in length.

FIGS. 4a-d illustrate various views of a base 16. FIG. 4a illustrates a front perspective view of base 16. FIG. 4b illustrates a right side view of base 16. FIG. 4c illustrates a top view of base 16. FIG. 4d illustrates a front view of base 16. Base 16 can be configured to support second component 14 as well as fluidly connect second component 14 to first component 12 and tank unit 20.

Base 16 can include a port 74 that can fluidly connect second component 14 to first component 12. In some embodiments, base 16 can include ports 76 and 78 that connect portions of second component 14 to respective conduits 46 and 50. In some embodiments, base 16 can include supports for supporting second component 14.

Figure 5B:
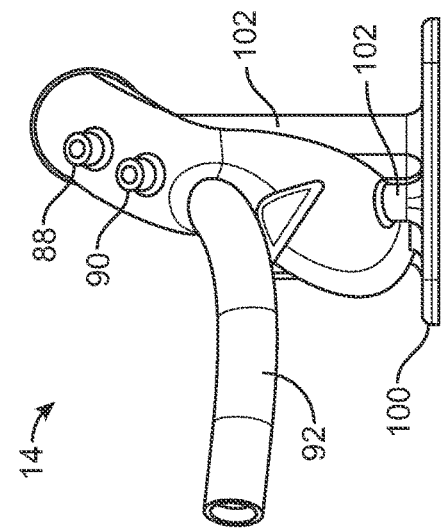
Figure 5D:
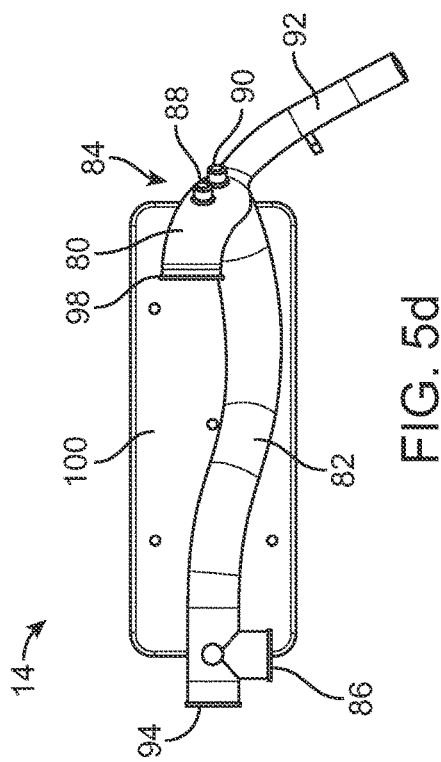
Figure 5A:
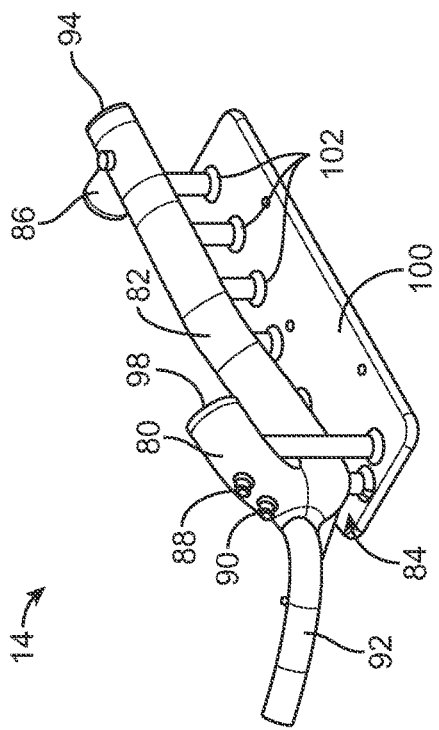
Figure 5C:
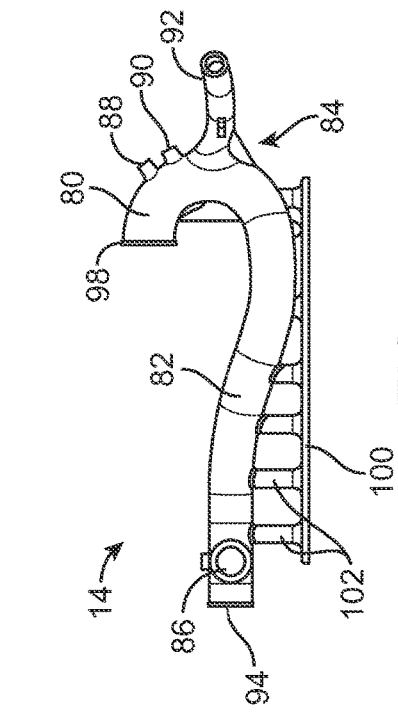

FIGS. 5a-d illustrate a second component 14. FIG. 5a illustrates a front perspective view of second component 14. FIG. 5b illustrates a left side view of second component 14. FIG. 5c illustrates a front view of second component 14. FIG. 5d illustrates a top view of second component 14. In some embodiments, second component 14 can be shaped to simulate anatomy. In some embodiments, second component 14 is not shaped to simulate anatomy. In some embodiments, second component 14 can simulate a portion of a patient's ascending aorta 80, as well as the descending aorta 82, and aortic arch 84. In some embodiments, a fluid outlet 86 can branch off from the descending aorta 82 and can be fluidly connected to a sealed tank, such as second tank 38 (in some embodiments), which in some embodiments can result in a simulation of arterial pressure.

In some embodiments, second component 14 is a thoracic aorta model and can include one or more portions simulating an ascending aorta, aortic arch, descending thoracic aorta, and/or related arteries.

In some embodiments, second component 14 can include one or more simulated arteries or outlets. In some embodiments, the arteries or outlets can be blocked off, which in some cases can allow for a simpler simulation. For example, in some embodiments, a brachiocephalic artery 88 and/or left common carotid artery 90 can be blocked off. In some embodiments, second component 14 can include one or more open arteries or portions thereof. For example, in some embodiments, second component 14 can include a simulated left subclavian artery 92.

In some embodiments, second component 14 can include a fluid outlet 94 that is fluidly connected to port 74 in base 16 and a fluid outlet 98 that is fluidly connected to third component 18.

In some embodiments, second component 14 can include a base 100 which can be configured to connect to base 16. In some embodiments, second component 14 can include one or more legs 102, which can support second component 14 and/or elevate second component 14 to a desired height or angle. In some embodiments, one or more legs 102 of second component 14 can be adjustable in length.

FIGS. 6a-c illustrate two embodiments of a third component. FIG. 6a illustrates a front perspective view of third component 18. FIG. 6b illustrates a front perspective view of another embodiment of a third component 18 having an alternative shape to the embodiment of FIG. 6a. FIG. 6c illustrates a rear perspective view of the third component 18 of FIG. 6b. In some embodiments, third component 18 is substantially hollow with relatively thin walls. In some embodiments, third component 18 can be shaped to simulate anatomy. In some embodiments, third component 18 can be based on the anatomy of a human cadaver. In some embodiments, third component 18 is not shaped to simulate anatomy.

In some embodiments, third component 18 includes a fluid outlet 109 that fluidly connects to port 78 of base 16. In some embodiments, third component 18 includes a fluid outlet 111 that fluidly connects to port 74 of base 16.

In some embodiments, third component 18 can be in the form of an anatomically correct flexible model of a left ventricle and aortic root ("LVAR"). In some embodiments, third component 18 can simulate an ascending aorta portion 107, as well as a left ventricle, aortic valve, and valve annulus. In some embodiments, third component 18 can include a sinus portion 104. In some embodiments, third component 18 can include one or more coronary arteries 106 and 108. In some embodiments, third component 18 can include a simulated version of the left side of the heart. Other portions of the heart or other anatomy can be used.

In some embodiments, third component 18 is constructed entirely or partially of a flexible material. In some embodiments, the flexible material can be a medical grade silicone (for example, NUSIL brand grade MED 10-6400 available from NuSil Technology LLC of Carpenteria, Calif., USA). In some embodiments, this material can have a durometer hardness measure of 30.

FIGS. 7a-d illustrate various views of tank unit 20. FIG. 7a illustrates a front perspective view of tank unit 20. FIG. 7b illustrates a top view of tank unit 20. FIG. 7c illustrates a left side view of tank unit 20. FIG. 7d illustrates a rear view of tank unit 20.

In some embodiments, tank unit 20 can include first tank 36 and second tank 38 disposed within a common housing 110. In some embodiments, first tank 36 and second tank 38 are disposed within separate housings. First tank 36 and second tank 38 can be separated by a wall 112 to prevent fluid from passing therebetween. In some embodiments, and as shown for example in FIG. 2, first tank 36 and second tank 38 can be fluidly connected via a conduit, such as conduit 56, or a port to allow fluid to pass therebetween if desired. Conduit 56 can include a valve 58, which can be in the form of an adjustable pinch clamp, which can restrict flow between first tank 36 and second tank 38. In some embodiments, a lower end 114 of first tank 36 is elevated relative to a lower end of second tank 38.

In some embodiments, first tank 36 can be open to the atmosphere at its upper end, as shown for example in FIG. 7a. Such a configuration can allow conduits within system 10, such as conduit 46 (which can allow for fast pacing) and conduit 50 (which can allow for variable back pressure) to be easily connected to first tank 36. First tank 36 can receive return flow from one or more conduits at its upper end and can be connected to a leg of T-junction 42 at its lower end through valve 44. In some embodiments, valve 44 can be disposed flush or nearly flush with the bottom surface of first tank. In some embodiments, valve 44 can be integrated with T-junction 42. In some embodiments, valve 44 and T-junction 42 can be separate components.

In some embodiments, one or both of first tank 36 and second tank 38 can include a drain valve (not illustrated in FIGS. 7a-d). The drain valve can be closed for filling one or both of the tanks and can be opened to drain one or both of the tanks.

In some embodiments, second tank 38 can be sealed to the atmosphere. In some embodiments, second tank 38 can function similar to a Windkessel, (which some in the art liken to an elastic reservoir that can provide variable compliance). In some embodiments, an amount of compliance of second tank 38 can be adjusted by adjusting an amount of fluid in second tank 38. In some embodiments, valve 58, which as described above can be in the form of an adjustable pinch clamp, can provide variable back pressure. In some embodiments, tank unit 20 can allow for accurate simulations of different hypertensive states of the body, such as for example systole and diastole.

In some embodiments, system 10 can include a pump 22. In some embodiments, pump 22 can be configured to ensure that an adequate amount of fluid is present before pump 22 operates. For example, pump 22 can include a float and/or a flow switch or other suitable devices.

The size and type of pump 22 can be selected to provide pressure and stroke volume in accordance with a desired simulation. For example, pump 22 can be a motor-driven reciprocating piston pump. In some embodiments, such a piston pump can allow for a flow of fluid in system 10 to regularly reverse direction. In some embodiments, pump 22 can be a pulse duplicator. In some embodiments, pump 22 can be a "Harvard pump", which is manufactured by Harvard Apparatus division of Harvard Bioscience Company. In some embodiments, pump 22 can be configured to provide a constant stroke volume. In some embodiments, a pump case of pump 22 can be waterproof. In some embodiments, pump 22 can include forward and reverse flow timing values of 50% each. In some embodiments, the timing values are not adjustable.

In some embodiments, system 10 can include one or more heaters to heat fluid within system 10. In some embodiments, pump 22 can include an integrated heater. In some embodiments, a heating control system can be contained inside a pump case of pump 22. One or more heaters can be used for example, to raise temperature of fluid within the system to a range of approximately 85° to approximately 100° F. In some embodiments, one or more of the components themselves can be heated to simulate a desired body temperature or other temperature.

In some cases, if the water is heated to simulate blood temperature, system 10 can include one or more resistance heaters in first tank 36. In some embodiments, such heaters can have sufficient capacity to heat a desired volume of available water to a desired temperature range in an acceptably brief time. In some embodiments, system 10 include additional or alternative heating devices. In some embodiments, system 10 can include one or more thermostatic temperature control and/or one or more thermometers which can indicate and/or control a fluid temperature. In some embodiments, pulsatile flow (including, if present, the heated fluid) can accurately replicate in vivo conditions of flow rate, pressure, and temperature. In some embodiments, each of these parameters can be adjusted or controlled to improve the accuracy of the simulation.

In some embodiments, a power supply can be used to operate pump 22. Suitable power supplies can include, for example, 120 VAC at 60 Hz or 240V at 50 Hz. In some embodiments, the power supply can power both a pump as well as one or more additional components of system 10. For example, a power supply can power a heater for heating fluid within tank unit 20. In some embodiments, a cardiac beat rate of system 10 can be set by a rate of pump 22. In some embodiments, a cardiac beat rate can be set by another device. In some embodiments, a cardiac output can be affected by one or more of total compliance, back pressure and stroke volume of pump 22. In some embodiments, pump speeds of 60 beats per minute to 100 beats per minute can be provided. This can allow for simulation of the following blood pressure states (per ISO 5840:2005 definitions for the left side heart): Normotensive (100 to 130 over 65 to 85 mmHg), Hypotensive (60 over 40 mmHg), Hypertensive Stage 1 (mild) (140 to 159 over 90 to 99 mmHg), Hypertensive Stage 2 (moderate) (160 to 179 over 100 to 109 mmHg), Hypertensive Stage 3 (severe) (180 to 209 over 110 to 119 mmHg).

System 10 can be configured to allow for simulated conditions of procedures. Examples of such simulated conditions can include simulated anatomy, body temperature, and/or hemodynamic parameters. In some embodiments, one or more of the internal surfaces of one or more components of system 10 can be treated to simulate the "feel" of a procedure. For example, system 10 can use water as a system fluid rather than actual blood. Although the fluid properties of water and blood are similar, the fluid properties are not identical. Given at least these differences between the simulation and an in vivo environment, the "feel" of the movement and placement of a device within the vasculature during a simulated procedure might not result in the same "feel" as an actual in vivo procedure even if the device itself is an actual implantable product.

In some embodiments, one or more components of system 10, such as third component 18, can be constructed from a silicone material. Some types of silicone material can be tacky as a result of relatively high coefficients of friction or other causes. Actual vasculature in a patient does not exhibit such tackiness. Therefore, in some embodiments, one or more internal surfaces of one or more components of system 10 can include a coating of material, such as for example silicone, liquid silicone rubber (LSR), or a suitable composition containing glass beads. In some cases, such a material can reduce tackiness and/or friction within the component. For example, in some embodiments, an inner surface adjacent to a simulated aortic valve is coated with such a material to reduce the surface friction. In some embodiments, the vasculature downstream of the valve, and also the regions where the vasculature is tortuous, such as the aortic arch to the aortic valve are coated in such a material. In some embodiments, regions where a delivery catheter would change direction from a linear path are coated in such a material.

In some embodiments, system 10 is configured to simulate the effects of calcification within the vasculature. For example, components manufactured by stereolithography can be configured to replicate a calcification profile and have that profile integrated a component of the system. In some embodiments, the stereolithography process can use a relatively rigid resin-based polymer. In some embodiments, the stereolithography process can use a semi-rigid polymer or other material.

In some embodiments, system 10 is configured to use anatomically-based delivery pathways between an access site and a target implant target location. In some embodiments, this can include a simulated functioning native valve and anatomy distal to the target implant location with which a delivery device can interact. In some embodiments, this can provide for a highly accurate simulation and training experience.

In some embodiments, system 10 is configured to allow for relatively easy removal of transcatheter valve implants from the anatomy. In some embodiments, this can allow for training to be rapidly repeated. In some embodiments, removal/restart cycle times can be on the order of 3-5 minutes.

The choice of materials for the components of the various physiologic simulator systems described herein can be informed by the requirements of mechanical properties, temperature sensitivity, biocompatibility, moldability properties, or other factors apparent to a person having ordinary skill in the art. For example, one or more of the components (or a portion of one of the components) can be made from suitable plastics, such as a suitable thermoplastic, suitable metals, and/or other suitable materials. One or more components of system 10 can be constructed entirely or partially of a flexible material. In some embodiments, the flexible material can be a medical grade silicone (for example, NUSIL brand grade MED 10-6400 available from NuSil Technology LLC of Carpenteria, Calif., USA). In some embodiments, one or more components can be constructed entirely or partially of actual human or another animal's anatomy. As merely one example, in some embodiments left subclavian artery 92 can be constructed partially or entirely from an actual human or another animal's left subclavian artery. In some embodiments, mammalian tissue (e.g., porcine aorta and heart, human cadaver heart) can be incorporated into one or more of the components.

Although this application describes a system 10 that can allow for certain procedures to be conducted with certain products, it should be noted that similar procedures for other products can be simulated by modifying the disclosed embodiments in accordance with known principles. For example, a lower pressure right side of a heart can be simulated by modifying system 10 to provide one or more of reduced back pressure, greater Windkessel volume, and less stroke volume. In some embodiments, this can obtain a wide variety of pressure states for the right side of the heart. Such configurations can allow for simulated implants of replacement pulmonary and/or tricuspid valves, or other procedures relevant to the anatomy of the right side of the heart.

In another example, a technique that can be used to bypass blockages in a left anterior descending coronary artery is revascularization via a left interior mammary artery (LIMA). Some embodiments of system 10 can enable training of procedures and/or devices for coronary revascularization and/or other interventional vascular procedures (e.g., endovascular abdominal aortic aneurysm grafting).

The foregoing description of the invention has been presented for purposes of illustration and description. It is not intended to be exhaustive or to limit the invention to the precise form disclosed. Other modifications and variations can be possible in light of the above teachings. The embodiments and examples were chosen and described in order to best explain the principles of the invention and its practical application and to thereby enable others skilled in the art to best utilize the invention in various embodiments with modifications as are suited to the particular use contemplated. It is intended that the appended claims be construed to include other alternative embodiments of the invention.

What is claimed is:

1. A system for the simulation of a percutaneous medical procedure, the system comprising:
   a simulated vasculature including
      a first component configured to allow for introduction of a medical device into the system through an introductory port,
      a second component connected to the first component and shaped to simulate a portion of a human vasculature, and
      a third component connected to the second component and shaped to simulate a delivery site for the simulated percutaneous medical procedure;
   a pump for pumping fluid through the simulated vasculature to simulate blood flow during the simulated percutaneous medical procedure; and
   a tank unit fluidly connected to the pump, wherein the tank unit includes a first tank that is unsealed and open to the atmosphere and a second tank that is sealed and not open to the atmosphere,
   wherein the system is configured to allow for a medical device to be delivered to the third component by passing through the introductory port of the first component and passing through the second component, and wherein the system is configured to replicate simulated conditions of use for the simulated percutaneous medical procedure, wherein the simulated conditions of use include simulated hemodynamic properties for the simulated percutaneous medical procedure.

2. The system of claim 1, wherein the simulated conditions of use further include simulated anatomy shape and size for the simulated percutaneous medical procedure.

3. The system of claim 1, wherein the first component is in the form of a simulated leg model to correspond to anatomy for the simulated percutaneous medical procedure.

4. The system of claim 1, wherein the first component includes a portion corresponding to a femoral artery to correspond to anatomy for the simulated percutaneous medical procedure.

5. The system of claim 1, wherein the second component includes a portion in the form of an aortic arch corresponding to anatomy for the simulated percutaneous medical procedure.

6. The system of claim 1, wherein the second component is in the form of a descending aorta, aortic arch, and a portion of the ascending aorta corresponding to anatomy for the simulated percutaneous medical procedure.

7. The system of claim 1, wherein a portion of the third component is in the form of an aortic valve corresponding to anatomy for the simulated percutaneous medical procedure.

8. The system of claim 1, wherein the third component is in the form of left ventricle, aortic valve, valve annulus, and a portion of the ascending aorta corresponding to anatomy for the simulated percutaneous medical procedure.

9. The system of claim 1, wherein the simulated conditions of use further include simulated body temperature for the simulated percutaneous medical procedure.

10. The system of claim 9, wherein one or more of the components of the system are heated to simulate a desired body temperature for the simulated percutaneous medical procedure.

11. The system of claim 9, wherein the fluid is heated to simulate a desired body temperature for the simulated percutaneous medical procedure.

12. The system of claim 1, wherein the simulated conditions of use further include simulated tackiness of one or more of the components to correspond to components of the simulated percutaneous medical procedure.

13. The system of claim 12, wherein an inner surface of one or more of the components is coated with a material to reduce friction of the inner surface.

14. The system of claim 13, wherein the inner surface is coated with silicone.

15. The system of claim 1, wherein the fluid is water for simulating blood for the simulated percutaneous medical procedure.

16. The system of claim 1, wherein the fluid is blood.

17. The system of claim 1, wherein the pump is configured to simulate fluid pressure within the system.

18. The system of claim 17, wherein the pump is configured to simulate one or more blood pressure states.

19. The system of claim 1, wherein the tank unit is configured to provide variable back pressure for one or more components in the system.

20. The system of claim 19, wherein the second tank has a variable compliance and includes a valve configured to permit an operator to vary an amount of fluid or pressure within the second tank in order to vary an amount of compliance of the second tank.

21. The system of claim 19, wherein the second component is fluidly connected to the first tank and the second tank and wherein the second tank is fluidly connected to the first tank via a conduit having a valve therein, the valve being configured to restrict the flow between the first tank and the second tank to provide a desired back pressure to the second component.

22. The system of claim 19, wherein the second component is fluidly connected to the first and second tanks and the second component is connected to the first tank via a conduit that is vertically oriented and sized to provide a desired back pressure to the second component.

23. The system of claim 1, wherein the simulated percutaneous medical procedure is a catheter-based implant procedure.

24. The system of claim 1, wherein the simulated percutaneous medical procedure is a catheter-based heart valve replacement procedure.

25. The system of claim 1, wherein the second component and the third component are a single monolithic component.

26. The system of claim 1, wherein the first component and the second component are a single monolithic component.

27. The system of claim 1, wherein the first component, the second component, and the third component are a single monolithic component.

28. The system of claim 1, wherein the first component includes legs that are sized to elevate the first component to a desired height or angle.

29. The system of claim 1, wherein the second component includes legs that are sized to elevate the second component to a desired height or angle.

30. The system of claim 1, wherein one or more of the components of the system is at least partially constructed of artificial materials.

31. The system of claim 1, wherein one or more components of the system is at least partially constructed from actual anatomy.

32. The system of claim 1, wherein one or more components of the system is transparent.

33. The system of claim 1, wherein one or more components of the simulated vasculature is configured to be disassembled and reassembled.

34. The system of claim 1, wherein the system is assembled for use on a table top.

35. The system of claim 1, wherein the simulated hemodynamic properties include a normal cardiac output and a reduced cardiac output.

36. A method of simulating a percutaneous medical procedure using a simulated vasculature including a first component configured to allow for introduction of a medical device into the system through an introductory port, a second component connected to the first component and shaped to simulate a portion of a human vasculature, a third component connected to the second component and shaped to simulate a delivery site for the simulated percutaneous medical procedure, the method comprising:
inserting the medical device into the introductory port of the first component;
advancing the medical device through the first component and into the second component;
advancing the medical device through the second component and into the third component; and
pumping fluid through the simulated vasculature to simulate blood flow during the simulated percutaneous medical procedure via a pump, wherein a tank unit is fluidly connected to the pump and the pump and the tank unit are configured to replicate simulated hemodynamic properties during the simulated percutaneous medical procedure, the tank unit including a first tank that is unsealed and open to the atmosphere and a second tank that is sealed and not open to the atmosphere.

37. The method of claim 36, further comprising:
delivering the medical device within the third component.

38. The method of claim 36, wherein the simulated percutaneous medical procedure simulates a transfemoral delivery procedure.

39. The method of claim 36, wherein the simulated percutaneous medical procedure simulates a transapical delivery procedure.

40. The method of claim 36, wherein the simulated percutaneous medical procedure simulates a transatrial delivery procedure.

41. The method of claim 36, wherein the simulated percutaneous medical procedure is a catheter-based implant procedure and the medical device includes a catheter.

42. The method of claim 37, further comprising:
retracting the medical device from the simulated vasculature.

43. The method of claim 36, further comprising:
varying a back pressure to the second component during the simulated percutaneous medical procedure.

44. The method of claim 36, further comprising:
varying a cardiac output to one or more components during the simulated percutaneous medical procedure.

* * * * *